April 4, 1972 W. T. PIPKIN Plant Pat. 3,100
PLUM TREE
Filed Nov. 21, 1968
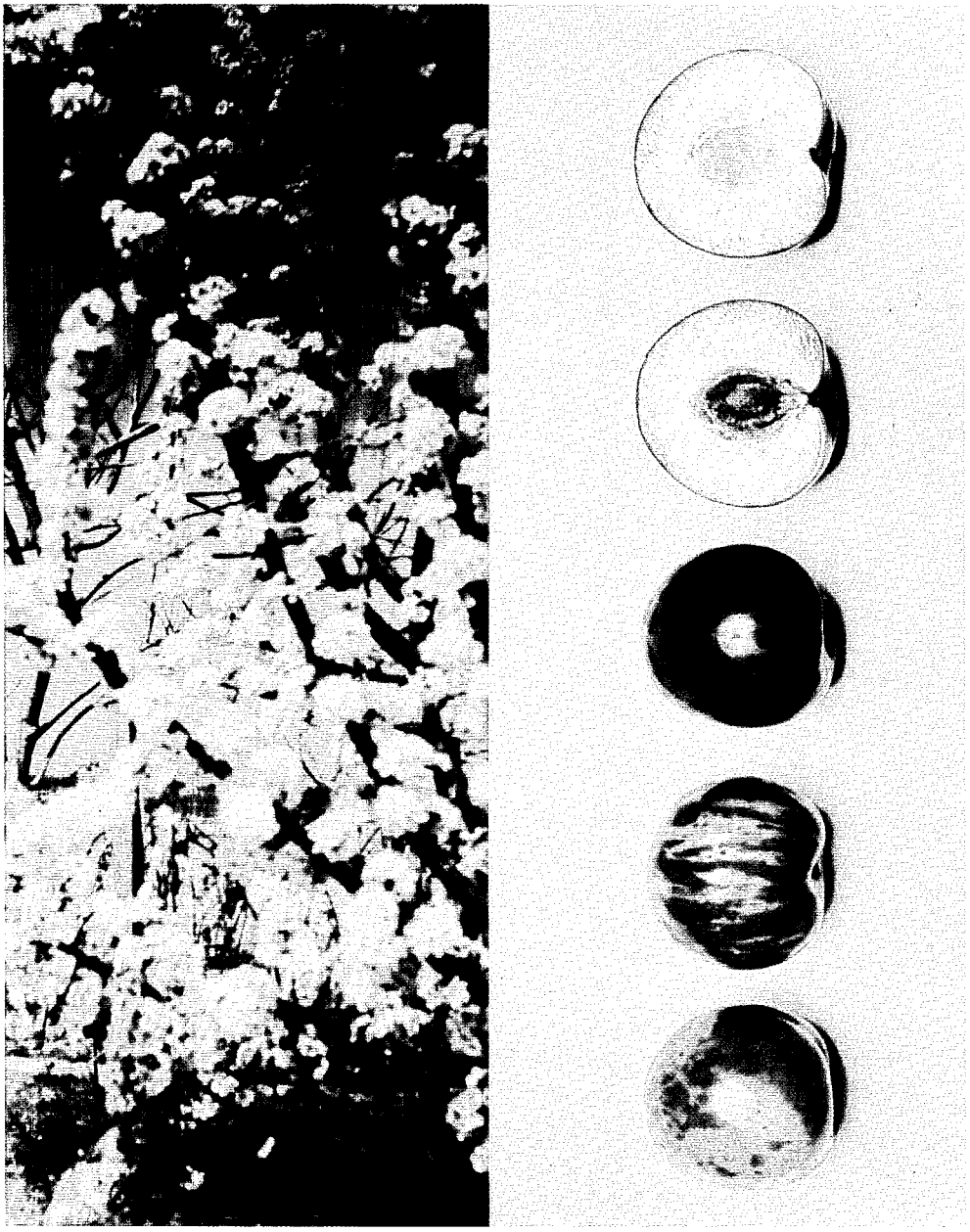
WILLIAM T. PIPKIN
INVENTOR
Huebner & Worrel
ATTORNEYS United States Patent Office Plant Pat. 3,100

Patented Apr. 4, 1972

3,100
PLUM TREE
Willilam T. Pipkin, 3193 W. Caruthers Ave.,
Caruthers, Calif. 93609
Filed Nov. 21, 1968, Ser. No. 777,925
Int. Cl. A01h 5/03
U.S. Cl. Plt.—38 1 Claim

ABSTRACT OF THE DISCLOSURE

The present invention relates to a new and distinct variety of plum tree broadly characterized by fruit having a distinctively striped skin and by blossoms significantly larger than the blossom of the unpatented Santa Rosa variety of plum which variety the instant variety most nearly resembles.

BACKGROUND OF THE INVENTION

While working at his ranch at 3193 W. Caruthers Ave., Caruthers, Calif., in the spring of 1964, namely between March and June of that year, the applicant noticed a new volunteer seedling growing on his ranch. The seedling was permitted to grow, and in 1965 the resulting tree blossomed and bore fruit. It was during the blossoming period in late February that the applicant noted that the blossoms of the discovered variety were significantly larger than the blossoms of the Santa Rosa plum tree, which was then blooming.

Subsequently, about the latter part of May, applicant noted other distinguishing characteristics in that the skin of the fruit had a dark red tiger-striped coloration. Later, it was noted that the fruit was of particularly good quality. The following year the applicant made cuttings from the parent tree and grafted them onto Santa Rosa root stock, as well as onto the root stock of the Lovell peach tree (unpatented) at his ranch. The grafts grew well and had the same characteristics as the parent tree.

SUMMARY OF THE INVENTION

The most significant features of the subject variety of plum tree includes its tiger-striped coloration. That is, the color is variegated and includes dark red stripes extending toward the base and superimposed on a strong orange-yellow background. The striping appears in the early stages of maturity as red spots or splotches on or against a yellow background and progressively develop into distinctive stripes which eventually expand so as substantially to cover the background, while remaining discernible, even at the late stages of maturity. Further, the fruit of the present variety of plums has a distinct apple flavor and has good keeping qualities. When compared to the Santa Rosa, the blossoms of the present variety are larger.

BRIEF DESCRIPTION OF THE DRAWING

The accompanying drawing illustrates typical specimens of the fruit taken during succeeding stages of maturity about the middle to the last of May, and typical blossoms taken during the blossoming period, about the latter part of February. The colors are as nearly true as is reasonably possible in color representation of this type.

DETAILED DESCRIPTION

Following is a detailed description of the characteristics of the subject fruit in accordance with the outline suggested by U. P. Hedrick in his book entitled "Systematic Pomology," published in 1925, and in accordance with the color terminology employed in the Nickerson Color Fan, distributed by American Horticultural Society and Published by the Munsell Color Co. Where dimension, sizes, color, or other characteristics are given, it is understood that such characteristics are approximations of averages set forth as accurately as practical.

Tree

The size of subject tree is similar to that of the Santa Rosa plum tree, however, the shape is considered to be more upright than spreading.

Productivity: Good.

Regularity of bearing: Very regular.

Trunk: The diameter in relation to length and the surface characteristics of the trunk are similar to those of the Santa Rosa plum tree.

Branches: The size and surface characteristics of the branches of subject tree are similar to those of the Santa Rosa. Color—A moderate reddish brown, 7.5R 3/6.

Leaves:

*Average size.*—Medium to large, similar to the Santa Rosa.

*Length.*—Approximately 5¾ inches.

*Width.*—Approximately 2 inches.

*Shape.*—Similar to the Santa Rosa.

*Color.*—A dark yellowish green, 10GY 4/5.

*Marginal form.*—Finely serrated.

*Petiole.*—Length—approximately 1⅛ inches; thickness—1/16 of an inch.

Flower buds: Similar to the Santa Rosa.

Flowers:

*Dates of bloom.*—About the same time as the Santa Rosa, mid to late February.

*Size and Color.*—Similar to Santa Rosa in color but significantly larger in size.

Fruit

Maturity: Matures early; that is, about the middle to the latter part of May in the San Joaquin Valley of California.

Size: Transverse diameter in the suture plane, approximately 1¾ inches; transverse diameter at right angle to the suture plane, approximately 2 inches.

Form: Generally uniform and spherical; symmetrical; suture, rather shallow, slightly deeper at the base and extending about 1½ inches along the suture plane; stem activity, elongated in the suture plane and relatively shallow; base, rounded; apex, rounded; stem length, medium length; and stem caliper, medium.

Skin: Medium thickness; smooth in texture; down-wanting color, dark red, 5R 3/7, stripes extending generally from the apex toward the base appearing against a background of strong orange-yellow, 7.5YR 7/11; the stripes first appear during early stages of maturity as large splotches of red against a yellow background, and progressively develop into distinctive stripes expanding into ever broadening stripes extending from the base to the apex, until at late maturity the stripes substantially obliterate the background, while yet remaining discernible as slightly darker red streaks of coloration against a slightly lighter red coloration.

Flesh: Color, vivid yellow 5Y 8/12; surface of pit cavity, medium; color of pit cavity, vivid yellow 2.5Y 8/12; juice, similar to the Santa Rosa; flavor, apple; aroma, slight; texture, juicy, but not mushy; fibers, few and fine; ripens evenly; excellent eating quality.

Stone: Free; fibers, few and fine; size, major axis approximately 1 inch by minor axis of ¾ of an inch in the suture plane by minor axis length of ⅜ of an inch at right angles to the suture plane; form, elliptic; apex, pointed; base, pointed; slightly furrowed at the base; color, very pale blue 10B 8/4.

Use: Eating, shipping, canning and marketing.

*Keeping quality.*—Very good.

*Shipping quality.*—Very good.

The new variety plum has been described as it exists under the ecological conditions prevailing in the central San Joaquin Valley of California. Normal variations can be expected under different environmental conditions.

Having thus described and illustrated my new variety of plum tree, what is claimed as new and desired to be secured by Letters Patent is:

1. A new and distinct variety of plum tree substantially as illustrated and described and being characterized by blossoms larger than the unpatented Santa Rosa and the bearing of large freestone fruit having a vivid yellow flesh and a tiger-striped skin of ever-broadening dark red stripes appearing against an ever-fading orange-yellow background and having a distinctive apple flavor.

No references cited.

ROBERT BAGWILL, Primary Examiner